(12) United States Patent
Reitmeier et al.

(10) Patent No.: US 9,829,457 B2
(45) Date of Patent: Nov. 28, 2017

(54) SENSOR ELEMENT AND A METHOD FOR DETECTING A PARAMETER OF A GAS MIXTURE IN A GAS CHAMBER

(75) Inventors: Torsten Reitmeier, Wackersdorf (DE); Andreas Wildgen, Nittendorf (DE)

(73) Assignee: Continental Automotive GmbH, Hannover (DE)

( * ) Notice: Subject to any disclaimer, the term of this patent is extended or adjusted under 35 U.S.C. 154(b) by 448 days.

(21) Appl. No.: 13/982,454

(22) PCT Filed: Jan. 26, 2012

(86) PCT No.: PCT/EP2012/051229
§ 371 (c)(1),
(2), (4) Date: Jul. 29, 2013

(87) PCT Pub. No.: WO2012/101212
PCT Pub. Date: Aug. 2, 2012

(65) Prior Publication Data
US 2013/0305812 A1    Nov. 21, 2013

(30) Foreign Application Priority Data

Jan. 28, 2011    (DE) ........................ 10 2011 009 780

(51) Int. Cl.
*G01N 27/30*    (2006.01)
*G01N 27/407*    (2006.01)
(Continued)

(52) U.S. Cl.
CPC ....... *G01N 27/304* (2013.01); *G01N 27/4067* (2013.01); *G01N 27/4071* (2013.01);
(Continued)

(58) Field of Classification Search
CPC ............. G01N 27/304; G01N 27/4072; G01N 27/4075; G01N 27/417; G01N 27/4071;
(Continued)

(56) References Cited

U.S. PATENT DOCUMENTS 4,272,350 A    6/1981    Croset et al.
4,595,485 A    6/1986    Takahashi et al.
(Continued)

FOREIGN PATENT DOCUMENTS

DE    31 08 305 A1    9/1982
DE    38 34 987 A1    4/1990
(Continued)

OTHER PUBLICATIONS

Office Action dated Jul. 11, 2014 issued in the corresponding Chinese Patent Application No. 2012800068997.

*Primary Examiner* — Randy Gibson
*Assistant Examiner* — Gedeon M Kidanu
(74) *Attorney, Agent, or Firm* — Cozen O'Connor (57) ABSTRACT

A sensor element for detecting a parameter of a gas mixture in a gas chamber, having a first electrode and a first diffusion barrier layer arranged to be coupled to said first electrode in a predetermined first region, and arranged such that the gas mixture of the gas chamber only impinges on the first electrode in the first region via the first diffusion barrier layer. In addition, the sensor element has a second electrode arranged such that the gas mixture of the gas chamber impinges on the second electrode in a further first region. The sensor element includes a solid electrolyte designed to be coupled to the first and the second electrodes.

15 Claims, 5 Drawing Sheets

(51) Int. Cl.
*G01N 27/419* (2006.01)
*G01N 27/417* (2006.01)
*G01N 27/406* (2006.01)

(52) U.S. Cl.
CPC ..... *G01N 27/4072* (2013.01); *G01N 27/4074* (2013.01); *G01N 27/417* (2013.01); *G01N 27/419* (2013.01)

(58) Field of Classification Search
CPC ........... G01N 27/4067; G01N 27/4074; G01N 27/419; H04N 19/117; H04N 19/147; H04N 19/176; H04N 19/51; H04N 19/82
USPC .................. 204/424; 427/125; 73/21, 31, 32
See application file for complete search history.

(56) References Cited

U.S. PATENT DOCUMENTS

| | | | | |
|---|---|---|---|---|
| 4,776,943 | A | 10/1988 | Kitahara | |
| 5,507,174 | A | 4/1996 | Friese et al. | |
| 5,997,707 | A * | 12/1999 | Kato | G01N 27/419 204/425 |
| 6,077,409 | A * | 6/2000 | Lee | G01N 27/4071 204/425 |
| 6,181,026 | B1 * | 1/2001 | Treharne | B60R 25/043 307/10.1 |
| 6,340,419 | B1 * | 1/2002 | Nakae | G01N 27/4071 156/89.12 |
| 6,471,840 | B1 | 10/2002 | Gao et al. | |
| 6,592,732 | B1 * | 7/2003 | Komachiya | G01N 27/419 204/408 |
| 6,916,415 | B2 | 7/2005 | Walde | G01N 27/4067 204/406 |
| 7,832,254 | B2 * | 11/2010 | Guenschel | G01N 15/0656 73/28.01 |
| 8,075,752 | B2 * | 12/2011 | Dalmia | G01N 27/4045 204/408 |
| 8,852,415 | B2 * | 10/2014 | Runge | G01N 27/4072 204/424 |
| 2003/0034246 | A1 * | 2/2003 | Liu | G01N 27/4071 204/424 |
| 2003/0121801 | A1 * | 7/2003 | Inaba | G01N 27/4075 205/785.5 |
| 2005/0043899 | A1 * | 2/2005 | Strassner | G01N 27/4065 702/24 |
| 2006/0137979 | A1 * | 6/2006 | Strassner | G01N 27/4071 204/424 |
| 2008/0047847 | A1 * | 2/2008 | Schmidt | G01N 15/0656 205/793 |
| 2008/0217174 | A1 * | 9/2008 | Kanters | G01N 27/4065 204/427 |
| 2009/0078025 | A1 * | 3/2009 | Singh | G01N 27/4073 73/31.04 |
| 2009/0114539 | A1 * | 5/2009 | Ziegler | G01N 27/4075 204/424 |
| 2009/0145778 | A1 * | 6/2009 | Allmendinger | G01N 27/419 205/789 |
| 2010/0000864 | A1 | 1/2010 | Diehl et al. | |
| 2010/0301871 | A1 * | 12/2010 | Biskupski | G01N 27/4075 324/464 |
| 2011/0015824 | A1 * | 1/2011 | Ante | F02D 41/1466 701/29.2 |
| 2011/0056270 | A1 * | 3/2011 | Reinhardt | G01N 27/4071 73/23.31 |
| 2011/0163314 | A1 * | 7/2011 | Park | G01N 27/4074 257/53 |
| 2013/0088807 | A1 * | 4/2013 | Tojo | H01T 23/00 361/231 |
| 2014/0262827 | A1 * | 9/2014 | Fix | G01N 27/30 205/775 |
| 2015/0293052 | A1 * | 10/2015 | Reinhardt | F02D 41/1454 205/781 |

FOREIGN PATENT DOCUMENTS

| | | |
|---|---|---|
| DE | 196 10 911 A1 | 9/1997 |
| DE | 697 14 112 T2 | 2/2003 |
| DE | 20 2004 015 400 U1 | 12/2004 |
| DE | 199 82 982 B4 | 10/2006 |
| DE | 10 2008 044 051 A1 | 5/2010 |
| EP | 0 152 942 A2 | 8/1985 |
| EP | 0 607 385 A1 | 7/1994 |
| JP | 55-82960 | 6/1980 |
| JP | 59-166854 | 9/1984 |
| JP | 60-173461 | 9/1985 |
| JP | 62-198748 | 9/1987 |
| JP | 06-160334 | 6/1994 |
| JP | 06-160341 | 6/1994 |
| JP | 07-501152 | 2/1995 |
| JP | 10-197477 | 7/1998 |
| JP | 2001-153837 | 6/2001 |
| JP | 2009-529689 | 8/2009 |

\* cited by examiner

SENSOR ELEMENT AND A METHOD FOR DETECTING A PARAMETER OF A GAS MIXTURE IN A GAS CHAMBER

CROSS REFERENCE TO RELATED APPLICATIONS

This is a U.S. national stage of application No. PCT/EP2012/051229, filed on Jan. 26, 2012. Priority is claimed on German Application No. DE102011009780.5 filed Jan. 28, 2011; the content of which is incorporated herein by reference.

BACKGROUND OF THE INVENTION

1. Field of the Invention

The invention relates to a sensor element and a method for the detection of a parameter of a gas mixture in a gas chamber.

2. Detailed Description of Prior Art

To detect an air/fuel mixture composition of an exhaust gas in an exhaust system of an internal combustion engine, modern motor vehicles comprise one or more solid state electrolyte sensors in the exhaust system. Such solid state electrolyte sensors are also referred to as lambda probes. The solid state electrolyte sensors each comprise a solid body with electrolytic properties, i.e. the solid body has the ability to electrically conduct certain ions. Lambda probes are known in numerous different embodiments.

DE 38 34 987 A1 discloses a sensor element for limiting current sensors for the determination of the lambda value of gas mixtures, especially the exhaust gases of internal combustion engines, with outer and inner pump electrodes disposed on an O-2 ion-conducting solid electrolyte, of which the inner pump electrode is accessible to the measurement gas passed through a diffusion gap and the diffusion gap is covered by the solid electrolyte, and in which the solid electrolyte forming the cover for the diffusion gap is a solid electrolyte layer formed by printing onto a ceramic carrier using screen printing technology.

DE 20 2004 015 400 U1 discloses a sensor both for oxygen measurement and for volumetric flow measurement and/or incident flow measurement, having on a region of a first surface of a plate-shaped support made of an electrical insulator successive layers of a solid state electrolyte, electrodes with connecting tracks and a diffusion barrier, which covers one of the electrodes up to its connecting track. A layer of an electrical conductor is disposed on a region of a second surface opposite the first surface of the plate-shaped support as at least one heating element.

EP 0 152 942 A2 discloses a device for the detection of an air-fuel ratio of a fuel mixture. The device comprises a partition with a first side and a second side. On the first side the partition bounds a volume that receives atmospheric air and that is pneumatically coupled to ambient atmosphere, and on the second side a volume that receives exhaust gases and that is pneumatically coupled to a source of the exhaust gases. The partition encloses at least one section of an oxygen ion-conducting solid state electrolyte. Furthermore, the device comprises a first electrode exposed to the atmospheric air, and a second electrode exposed to the exhaust gas, wherein the oxygen ion-conducting solid state electrolyte is disposed between the first and second electrode. Furthermore, the a device comprises a limiter to limit the gas diffusion of the exhaust gases to the gas-receiving volume.

DE 31 08 305 A1 discloses a polarographic measurement sensor for the determination of the lambda equivalence point in exhaust gases, which operates according to the diffusion limit current principle, with an oxygen ion-conducting solid electrolyte body in the form of a small plate that carries an anode on one side and a cathode on the other side, to which a constant voltage can be applied. The cathode is covered by a diffusion barrier in the form of a porous layer and both electrodes are exposed to the gas to be measured. The cathode is divided into two partial cathodes, which are juxtaposed in the measurement region, and that one partial cathode is more cathodically polarized than the second partial cathode.

EP 0 607 385 A1 discloses a sensor for the determination of the concentration of specified components in the exhaust gas of internal combustion engines. The sensor comprises a pump cell whose cathode is provided with a first diffusion barrier and whose anode is provided with a second diffusion barrier. In an alternative embodiment the sensor comprises a reference electrode that is not loaded in the measurement gas for measuring the polarization of at least one of the electrodes relative to said reference electrode.

DE 196 10 911 A1 discloses a device for the determination of the partial pressure of a gas in a gas mixture, especially in air, with a gas sensor comprising a measurement chamber with a wall formed by a solid electrolyte and comprising at least one pair of electrodes, whose inner electrode is disposed in the measurement chamber and whose other outer electrode is in contact with the gas mixture. Furthermore, the device comprises a control unit, which is provided to apply a pump voltage to a pair of electrodes associated with the solid electrolyte during operation to generate a pump current. The control unit interrupts the pump current at times. Furthermore, the device comprises a measurement unit, which during the no-current period measures the potential difference between an electrode pair associated with the solid electrolyte, the potential difference being produced by a Nernst voltage.

SUMMARY OF THE INVENTION

An object of the invention is to provide a sensor element and a method for the detection of the parameter of the gas mixture in the gas chamber can detect the parameter reliably and precisely.

According to one embodiment of the invention a sensor element for the detection of a parameter of a gas mixture in a gas chamber comprises a first electrode and a first diffusion barrier layer, which is disposed so that it is coupled to the first electrode in a specified first region and the first electrode is only acted upon by the gas mixture of the gas chamber in the first region via the first diffusion barrier layer. Furthermore, the sensor element comprises a second electrode, which is disposed so that it is acted upon by the gas mixture of the gas chamber in another first region. The sensor element comprises a solid state electrolyte that is designed so that it is coupled to the first and second electrodes.

The solid state electrolyte is in particular mechanically coupled to the first electrode and the second electrode. The solid state electrolyte is preferably designed such that it can electrolytically transport oxygen ions in a specific operating temperature range. Advantageously, the sensor element according to one embodiment of the invention can be manufactured inexpensively. Furthermore, it can make a contribution to increasing the service life and reliability of the sensor element, because the sensor element enables a layered construction without cavities and/or gas flow channels. For a sensor device in which the first electrode is acted upon by the gas mixture of the gas chamber via a gas inlet limiter with a cavity and/or a gas flow channel, e.g. a condensate can penetrate into the cavity and/or into the gas flow channel. Because the sensor device is exposed to large temperature fluctuations, there can be thermomechanical stresses, e.g. in the solid state electrolyte enclosing the respective cavity. The thermomechanical stresses can lead to damage to the sensor device.

In one advantageous embodiment the first diffusion barrier layer comprises a porous ceramic material.

In another advantageous embodiment the first diffusion barrier layer comprises zirconium dioxide.

In another advantageous embodiment the first electrode and the second electrode are disposed on the same side of the solid state electrolyte. This enables inexpensive manufacture of the sensor element. The sensor element can hereby have e.g. a planar layer construction or a circular cylindrical layer construction.

In another advantageous embodiment the first electrode and the second electrode are spaced apart in a specified manner along a first axis and along a second axis, is the second axis being orthogonal to the first axis, vertically offset with respect to each other and at least partly embedded in the solid state electrolyte. This enables the first region of the first electrode and the other first region of the second electrode to be disposed in relation to the second axis and vertically offset with respect to each other.

In another advantageous embodiment of the invention the gas inlet limiter comprises a first diffusion barrier layer that is disposed such that it is coupled to the first electrode in a specified first region and the first electrode is acted upon by the gas mixture of the gas chamber via the diffusion barrier layer only in the first region.

In another advantageous embodiment the sensor element comprises a second diffusion barrier layer. The second diffusion barrier layer is disposed in such a way that it is coupled in the other first region to the second electrode and the second electrode in the other first region is acted upon by the gas mixture of the gas chamber via the second diffusion barrier layer. The second diffusion barrier layer has a second diffusion resistance for at least one specified gas component of the gas mixture, which is lower than a first diffusion resistance of the first diffusion barrier layer. The second diffusion resistance for the specified gas component is preferably significantly lower than the first diffusion resistance. Preferably, the gas component comprises oxygen molecules. The second diffusion barrier layer can e.g. be designed to shield the second electrode against oxidizable gas components, e.g. hydrocarbon and hydrogen molecules.

In another advantageous embodiment the first and the second diffusion barrier layers comprise the same ceramic material. This enables simple manufacture of the sensor element.

In another advantageous embodiment the other first region of the second electrode has a larger area than the first region of the first electrode.

According to one embodiment of the invention a method for the detection of a parameter of a gas mixture in a gas chamber with a sensor element, which is disposed in the gas chamber and whose first and second electrodes are electrically coupled to a power supply comprises the following steps:

During a measurement phase the power supply is driven so as to shut down;

During the measurement phase an electrode voltage between the first and second electrodes is detected and a pump current is determined depending on a deviation of said electrode voltage from a predefined target voltage; and In an operating phase that follows the measurement phase in time, the power supply is controlled such that that it outputs the pump current to the second electrode of the sensor element.

The steps of the measurement phase and the subsequent control of the power supply to output the pump current to the second electrode are carried out multiple times to minimize the deviation between the electrode voltage and the specified target voltage. The parameter of the gas mixture in the gas chamber is determined depending on the pump current.

For example, the measurement phase can have a specified constant first time duration and the operating phase can have a constant specified second time duration and the measurement phase and the operating phase are cyclically repeated. Preferably, a repeat measurement phase follows immediately after the operating phase, which follows a preceding measurement phase. However, the operating phase can be interrupted, e.g. for one or more further phases for the detection of other operating variables, for example for the detection of a pump voltage. The parameter of the gas mixture is determined depending on the pump current e.g. if in one or more immediately successively following measurement phases the deviation between the electrode voltage and the target voltage is essentially equal to zero. During the measurement phase the power supply is controlled to switch off so that the power supply outputs essentially no current, particularly no current to the sensor element. The electrode voltage detected during the measurement phase can represent a Nernst voltage. The method according to one embodiment of the invention can thus make a contribution to determining the parameter of the gas mixture in the gas chamber precisely and reliably, preferably to determine an oxygen concentration of the gas mixture precisely and reliably. Furthermore, by operating the sensor element with a controlled power supply the service life of the solid state electrolyte and hence of the sensor element can be increased in comparison to the amperometric operation of the sensor element. With amperometric operation a specified voltage is applied to the first and second electrodes and a current flowing between the two electrodes is detected. With amperometric operation of the sensor element, especially if there are no or very few oxygen molecules on the second electrode, an electric field that is produced in the solid state electrolyte by the voltage applied to the first and second electrodes can cause the zirconium dioxide of the solid state electrolyte to be at least partially decomposed and hence after a certain time the solid state electrolyte loses its electrolytic properties. Advantageously, the sensor element with only two electrodes is sufficient for the determination of the parameter. A reference channel and/or a reference electrode for an oxygen supply are not necessary for this. The number of supply lines to the sensor element can thus likewise be kept small.

According to one embodiment of the invention a method for the detection of a parameter of a gas mixture in a gas chamber with a sensor element, which is disposed in the gas chamber and whose first and second electrodes are electrically coupled to a power supply and the sensor element comprises a first electrode and a gas inlet limiter, which is disposed and designed so that the first electrode is acted upon by the gas mixture of the gas chamber in a specified first region above the gas inlet limiter. Furthermore, the sensor element comprises a second electrode, which is disposed so that it is acted upon by the gas mixture of the gas chamber in another first region. The sensor element comprises a solid state electrolyte, which is designed so that it is coupled to the first and second electrodes. The method hereby comprises the following steps:

During a measurement phase the power supply is controlled to switch off;

During the measurement phase an electrode voltage between the first and second electrodes is detected and a pump current is determined depending on a deviation of the electrode voltage from a specified target voltage; and In an operating phase, which follows the measurement phase in time, the power supply is controlled such that it outputs the pump current to the second electrode of the sensor element. The steps of the measurement phase and the subsequent control of the power supply to output the pump current to the second electrode are carried out multiple times so as to minimize the deviation between the electrode voltage and the specified target voltage.

The parameter of the gas mixture in the gas chamber is determined depending on the pump current.

Advantageously, the parameter of the gas mixture can thus be detected using a sensor device, whereby the sensor element comprises the two electrodes, the solid state electrolyte and the gas inlet barrier, wherein the gas inlet barrier comprises a channel and/or a chamber. The channel or the chamber can e.g. comprise an additional diffusion barrier, which is disposed and designed to restrict the penetration of the gas mixture of the gas chamber into the chamber or into the channel.

In one advantageous embodiment of the invention the sensor element comprises a heating element for heating the solid state electrolyte. The heating element is controlled during the measurement phase so as to switch off and during the operating phase the heating element is controlled so as to set a specified operating temperature of the solid state electrolyte. This enables the electrode voltage, which can represent the Nernst voltage, to be precisely detected.

The solid state electrolyte is in particular mechanically coupled to the first electrode and the second electrode. The solid state electrolyte is preferably designed in such a way that it can electrolytically transport oxygen ions in a specific operating temperature range. Advantageously, the sensor element according to the invention can be manufactured inexpensively. Furthermore, it can make a contribution to increasing the service life and reliability of the sensor element, because the sensor element enables a layered construction without cavities and/or gas flow channels. For a sensor device in which the first electrode is acted upon by the gas mixture of the gas chamber via a gas inlet limiter with a cavity and/or a gas flow channel, e.g. a condensate can penetrate into the cavity and/or into the gas flow channel. Because the sensor device is exposed to large temperature fluctuations, there can be thermomechanical stresses, e.g. in the solid state electrolyte enclosing the respective cavity. The thermomechanical stresses can lead to damage to the sensor device. By the vertically offset arrangement of the first and second electrodes, the first region of the first electrode and the other first region of the second electrode can be disposed vertically offset with respect to each other in relation to the second axis.

In another advantageous embodiment of the invention the parameter represents an oxygen concentration of the gas mixture.

In another advantageous embodiment of the invention the gas chamber is an induction chamber of an internal combustion engine.

BRIEF DESCRIPTION OF THE DRAWINGS

Example embodiments of the invention are explained below using the schematic figures.

In the figures.

Elements of the same design or function are provided with the same reference characters in all figures.

DETAILED DESCRIPTION OF THE PRESENTLY PREFERRED EMBODIMENTS

Figure 1:
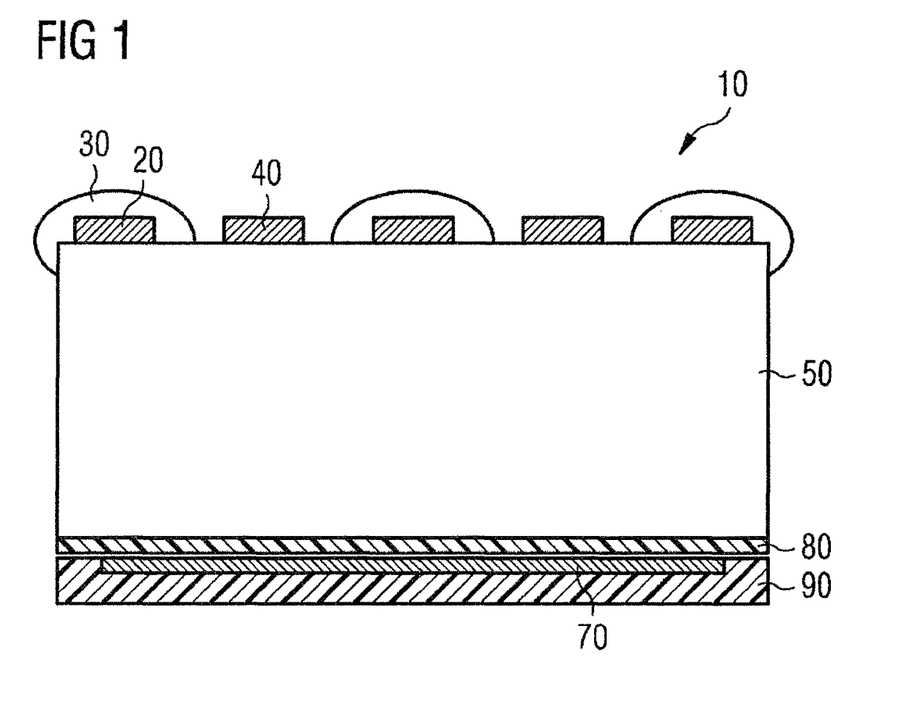
FIG. 1 is a sectional view of a first example embodiment of a sensor element for the detection of a parameter of a gas mixture in a gas chamber.

FIG. 1 shows a first example embodiment of a sensor element 10 for the detection of a parameter of a gas mixture in a gas chamber.

The sensor element 10 can be disposed in a motor vehicle at one or more positions. For example, the sensor element 10 can be disposed at one or more positions in an induction tract of an internal combustion engine of the motor vehicle or in an induction chamber of the induction tract.

The sensor element 10 can be used to determine an oxygen concentration in the induction tract downstream of an opening of an exhaust gas return. Alternatively or additionally, the sensor element 10 can be disposed in an exhaust system of an internal combustion engine. Preferably, the sensor element 10 can be used in an environment with an oxygen concentration of approximately greater than 2%, especially greater than 5%.

The sensor element 10 comprises a first electrode 20 and a first diffusion barrier layer 30, which is disposed such that it is coupled to the first electrode 20 in a specified first region and the first electrode 20 is acted upon by the gas mixture of the gas chamber only in the first region above the first diffusion barrier layer 30. Furthermore, the sensor element 10 comprises a second electrode 40, which is disposed such that it is acted upon by the gas mixture of the gas chamber in another first region. Furthermore, the sensor element 10 comprises a solid state electrolyte 50, which is designed such that it is coupled to the first 20 and second 40 electrodes. The solid state electrolyte 50 can e.g. comprise yttrium-stabilized zirconium dioxide (YSZ). The first electrode 20 and the second electrode 40 can comprise, for example, a precious metal, for example platinum, palladium, iridium, tantalum, or a combination of said metals. With the sensor element 10 shown in FIG. 1 the first electrode 20 and the second electrode 40 are disposed on a common side of the solid state electrolyte 50. The sensor element 10 can e.g. have a planar layer construction. The sensor element 10 can e.g. comprise a protective layer 90. For example, a heating element 70 can be embedded in the protective layer 90. E.g. thermal insulation 80 can be disposed between the heating element 70 and the solid state electrolyte 50. The heating element 70 can e.g. be used to set a working temperature of the solid state electrolyte 50.

Figure 2:
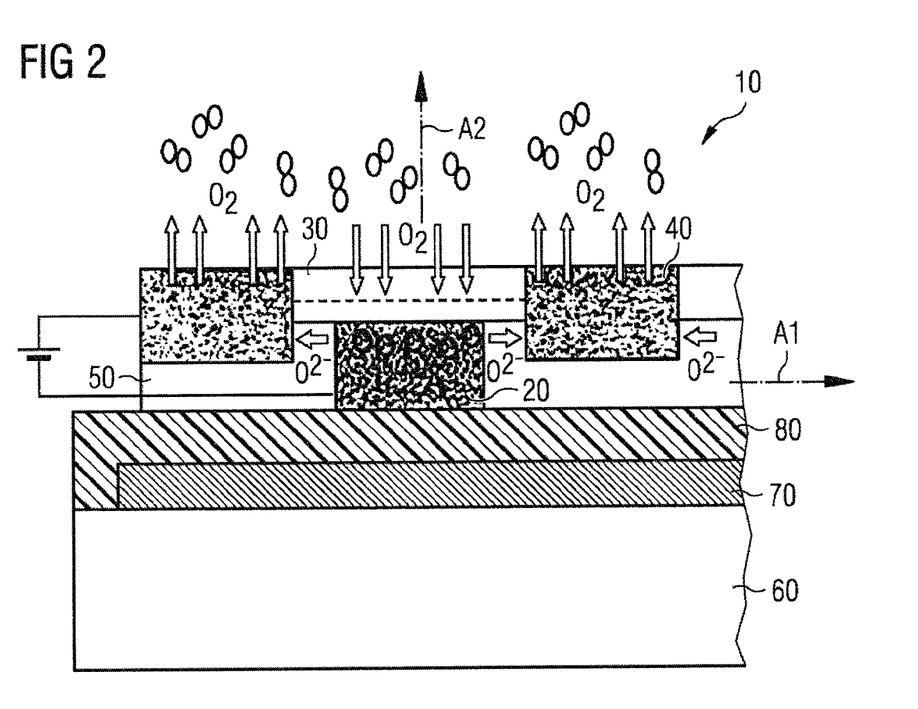
FIG. 2 is a sectional view of a second example embodiment of the sensor element for the detection of the parameter of the gas mixture in the gas chamber.

In the example embodiment of the sensor element 10 shown in FIG. 2, the first electrode 20 and the second electrode 40 are placed at specified intervals along a first axis A1 and along a second axis A2 that is orthogonal to the first axis A1, are vertically offset relative to each other and at least partly embedded in the solid state electrolyte 50. The sensor element 10 can comprise the support 60, the heating element 70 and the thermal insulation 80, which can be in the form of planar layers. The thermal insulation 80 can be disposed between the heating element 70 and the solid state electrolyte 50.

Figure 3:
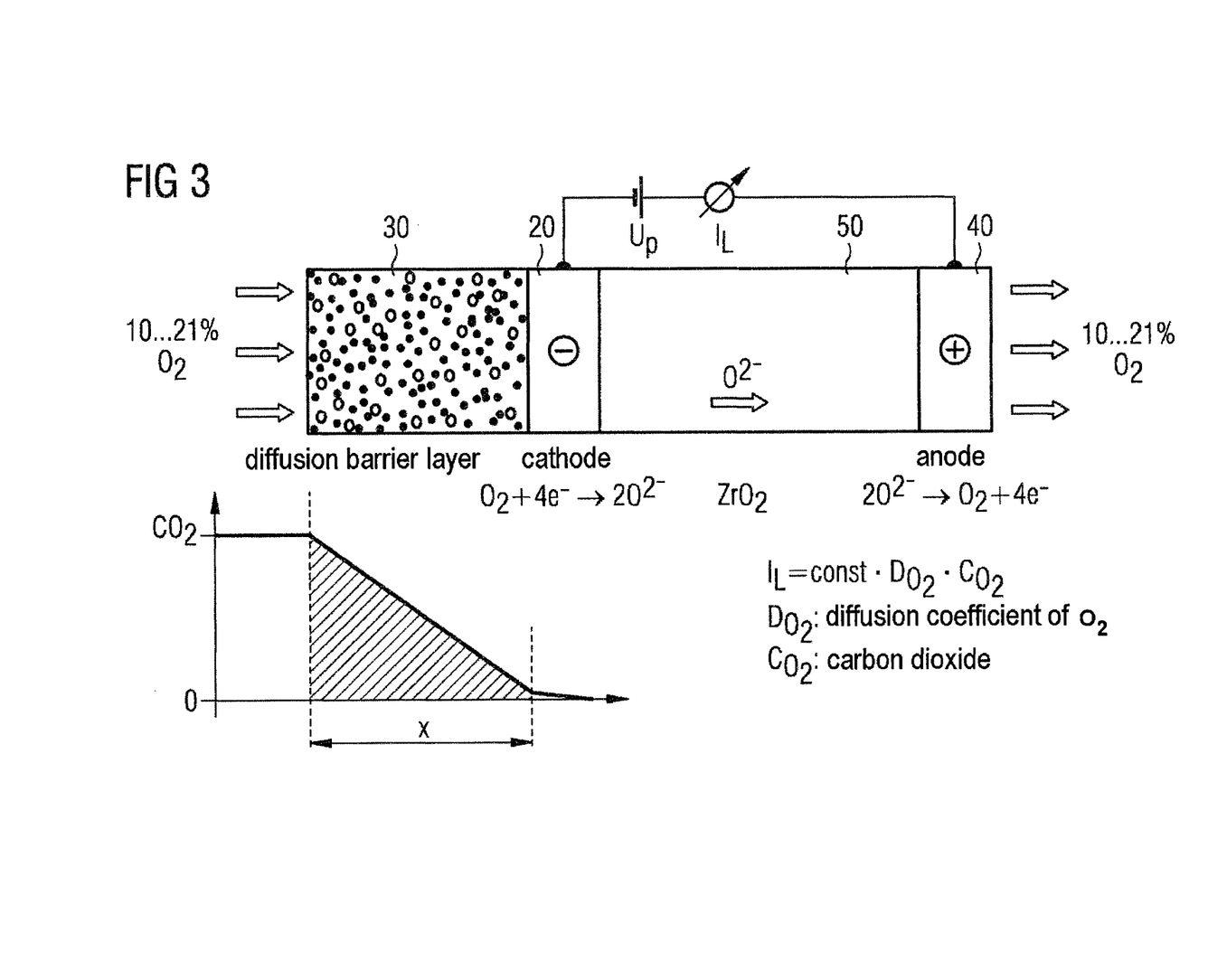
FIG. 3 is an illustration of the principle of the transportation of oxygen ions through a solid state electrolyte.

FIG. 3 shows an illustration of the principle of the transportation of oxygen ions through the solid state electrolyte 50. The gas chamber, e.g. the induction chamber of the internal combustion engine, in which the sensor element 10 can be disposed, has e.g. an oxygen concentration of >2%, for example an oxygen concentration of approximately 10% to 20%. The oxygen contained in the gas mixture diffuses across the diffusion barrier layer to the first electrode 20.

The diffusion barrier layer comprises a specified first diffusion resistance.

Advantageously, the sensor element 10 is operated during an operating phase such that the first electrode 20 is operated as a cathode and the second electrode 40 as an anode. For this purpose the first 20 and second 40 electrodes are electrically coupled to a power supply, or alternatively to a voltage source, such that the second 40 electrode has an anode function and the first electrode 20 has a cathode function. If a lean gas mixture passes through the diffusion barrier layer, oxygen molecules at the first electrode 20 are electrochemically reduced to oxygen ions. At the first electrode 20, which has the cathode function, an oxygen molecule acquires four electrons. Thus two oxygen ions are formed from each oxygen molecule. The solid state electrolyte 50 comprises e.g. zirconium dioxide, which is doped with yttrium oxide ($Y_2O_3$). Doping-related defect points in a grid structure of the zirconium dioxide enable the oxygen ions to diffuse through the solid state electrolyte 50. The negative oxygen ions are drawn in by the first electrode 20 and recombined at the second electrode 40. The first electrode 20 and the second electrode 40 can comprise a porous precious metal, e.g. the electrodes 20, 40 can comprise a cermet material.

A dark current of oxygen molecules is limited by the first diffusion barrier layer 30 or a differently designed gas inlet barrier. By the controlled transport of oxygen ions away from the first electrode 20 the oxygen concentration at the first electrode 20 reduces to approximately 0. Thus a reference gas environment can be set up at the first electrode 20 with an oxygen concentration of 0%, which corresponds to an air ratio of 1 ($\lambda=1$).

The sensor element 10 is operated during the operating phase in limiting current mode. In said limiting current mode a pump current, which is required to set the reference gas environment at the first electrode 20 with $\lambda=1$, depends on the oxygen concentration in the gas chamber. The oxygen concentration in the gas chamber can e.g. be determined depending on a specified characteristic.

Figure 4:
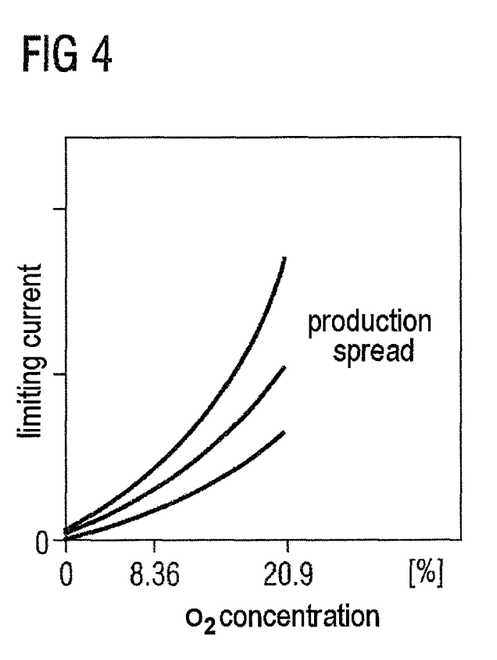
FIG. 4 is a pump current/oxygen concentration characteristic field.

FIG. 4 shows such a pump current/oxygen concentration characteristic diagram for the limiting current mode for the sensor element 10.

For the detection of a parameter of a gas mixture in a gas chamber with the sensor element 10 the sensor element 10 disposed in the gas chamber with the first electrode 20 and the second electrode 40 can be electrically coupled to a power supply. During a measurement phase the power supply is controlled so as to switch off. Thus during the measurement phase essentially no pump current is flowing. The heating element 70 of the sensor element 10 is likewise controlled so as to switch off during the measurement phase. During the measurement phase an electrode voltage between the first 20 and second 40 electrodes is detected and a pump current is determined depending on a deviation of the electrode voltage from a specified target voltage. The measurement phase can last for 1 ms. The first 20 and second 40 electrodes have a potential difference as a result of the different partial oxygen pressures on the two electrodes 20, 40, which is also referred to as a Nernst voltage. If the pump current remains turned off for a longer time, the partial oxygen pressures of the first 20 and second electrodes 40 equalize, i.e. the Nernst voltage reduces. The Nernst voltage can be measured in the measurement phase, when essentially no pump current is flowing. During the operating phase, with the pump current actively supplied into the sensor element 10, a pump voltage is applied between the first 20 and second 40 electrodes, which represents the sum of the Nernst voltage and a product of the pump current and a cell impedance between the first 20 and second 40 electrodes.

The Nernst voltage can be used to regulate the pump current so that the reference gas environment with $\lambda=1$ remains at least approximately the same at the first electrode 20. Because the sensor element 10 is preferably used in an environment in which the gas mixture has an oxygen concentration of at least greater than 2%, especially greater than 5%, the second electrode 40 is adequate as a reference electrode relative to the first electrode 20 to provide a uniform reference gas environment at the first electrode 20. In comparison to an ideal reference electrode, which is disposed in an air channel with essentially 21% oxygen concentration, if the oxygen concentration is 0% on the first electrode 20, the measured Nernst voltage is only slightly different.

Figure 5:
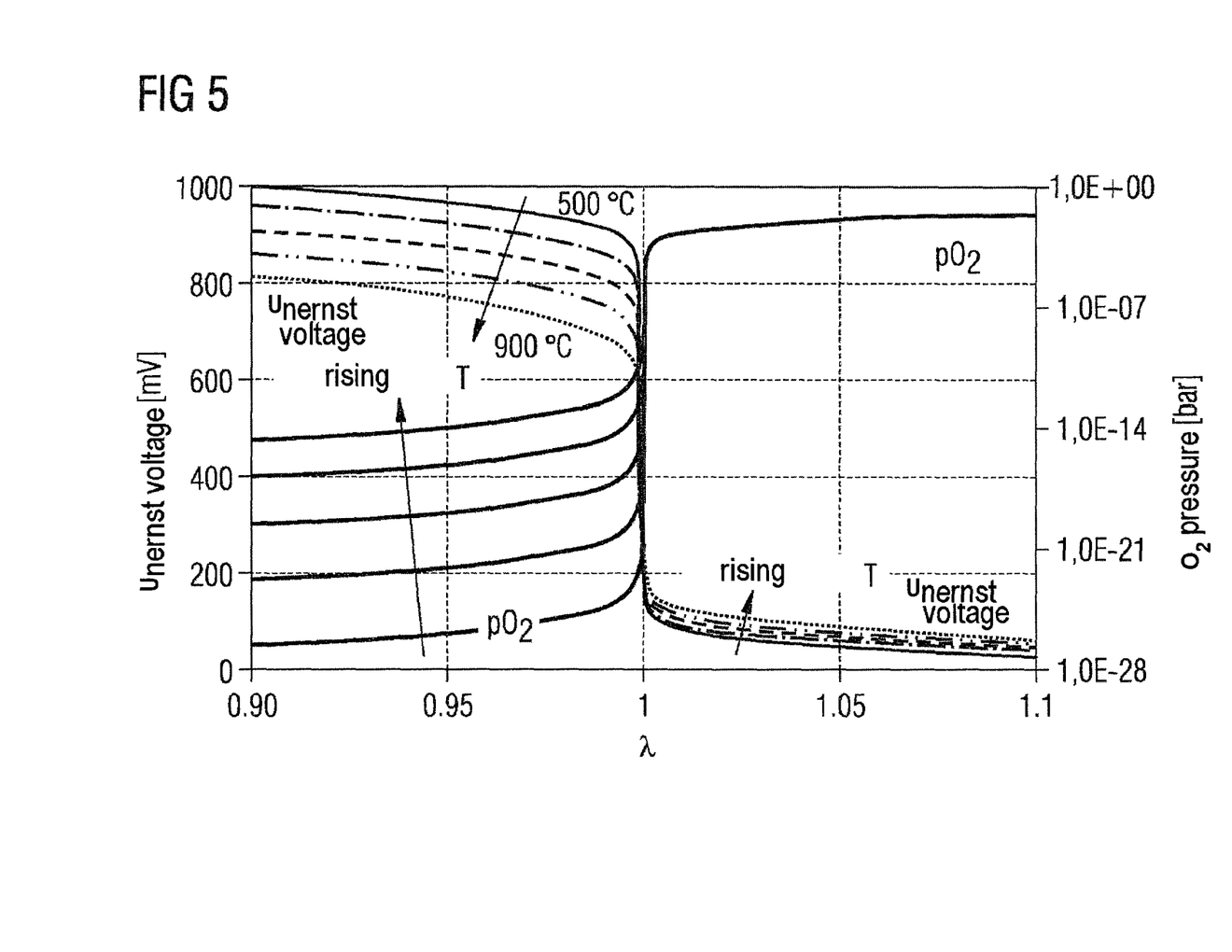
FIG. 5 is a Nernst voltage diagram.

FIG. 5 shows a Nernst voltage diagram. A change of the oxygen concentration in the gas mixture initially results in the oxygen concentration on the first electrode 20 changing and the detected Nernst voltage changing. Depending on the deviation of the detected Nernst voltage from the specified target value, which can be e.g. 400 mV, the pump current can be adapted so that the reference gas environment on the first electrode 20 can be reset to 0% oxygen concentration.

For this purpose in the operating phase, which follows the measurement phase in time, the power supply is controlled such that it outputs the pump current to the second electrode 40 of the sensor element 10. The sensor element is operated in the limiting current mode. During the operating phase the heating element 70 is controlled so as to set up a specified operating temperature of the solid state electrolyte 50. The operating temperature can be 650° C. The operating phase can last for e.g. 4 ms. The steps of the measurement phase and the following control of the power supply to output the pump current to the second electrode 40 are carried out multiple times to minimize the deviation between the electrode voltage and the specified target voltage. The parameter of the gas mixture in the gas chamber is determined depending on the pump current. The parameter is determined in each case if it is detected that the deviation between the detected electrode voltage and the target voltage is minimal. For example, the oxygen concentration of the gas mixture can be determined depending on the specified characteristic, which characterizes the dependency of the pump current on the oxygen concentration in the limiting current mode of the sensor element 10.

In addition it is possible to vary the target voltage in specified time intervals. For example, if the operating phase lasts for 4 ms and the measurement phase lasts for 1 ms, the target voltage is changed over between a first and a second voltage value every second. This has the advantage that polarization effects in the solid state electrolyte 50 can be kept lower.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A sensor element configured to detect a parameter of a gas mixture in a gas chamber, comprising:
   a first electrode;
   a first diffusion barrier layer disposed such that it is coupled to the first electrode in a specified first region, wherein the first electrode is acted upon by the gas mixture of the gas chamber via the first diffusion barrier layer only in the first region;
   a second electrode disposed such that it is acted upon directly by the gas mixture in another first region; and
   a solid state electrolyte coupled to the first and second electrodes,
   wherein the sensor element has a planar layered structure, the first electrode and the second electrode being spaced apart along a first axis at specified intervals so that their respective edges are spaced apart from each other along the first axis and along a second axis that extends orthogonally to the respective layers and orthogonally to the first axis, are vertically offset relative to each other, and at least partly embedded in the solid state electrolyte, and
   wherein one surface of the second electrode and one surface of the first diffusion barrier layer form a plane, via which the second electrode is acted upon directly by the gas mixture of the gas chamber and via which the first electrode is indirectly acted upon by the gas mixture of the gas chamber via the first diffusion barrier layer.

2. The sensor element as claimed in claim 1, wherein the first diffusion barrier layer comprises zirconium dioxide.

3. The sensor element as claimed in claim 1, wherein the another first region of the second electrode has a larger area than the first region of the first electrode.

4. The sensor element as claimed in claim 1, further comprising:
   a heating element configured to heat the solid state electrolyte, wherein
   the heating element configured to be controlled during a measurement phase to switch off and
   during an operating phase the heating element is configured to be controlled to set up a specified operating temperature of the solid state electrolyte.

5. The sensor element as claimed in claim 1, wherein the first diffusion barrier layer comprises a porous ceramic material.

6. The sensor element as claimed in claim 5, wherein the first diffusion barrier layer comprises zirconium dioxide.

7. The sensor element as claimed in claim 1, further comprising a second diffusion barrier layer disposed such that it is coupled in the another first region to the second electrode and the second electrode is acted upon by the gas mixture of the gas chamber only in the another first region via the second diffusion barrier layer,
   wherein the second diffusion barrier layer has a second diffusion resistance for at least one specified gas component of the gas mixture that is lower than a first diffusion resistance of the first diffusion barrier layer.

8. The sensor element as claimed in claim 7, wherein the first diffusion barrier layer and the second diffusion barrier layer comprise a same ceramic material.

9. A method for detecting of the parameter of the gas mixture in a gas chamber with a sensor element as claimed in claim 1 that is disposed in the gas chamber and whose first and second electrodes are electrically coupled to a power supply, comprising:
   controlling the power supply to switch off during a measurement phase;
   detecting an electrode voltage between the first and second during the measurement phase;
   determining a pump current based at least in part on a deviation of the electrode voltage from a specified target voltage during the measurement phase;
   controlling the power supply to output the pump current to the second electrode of the sensor element in an operating phase that follows the measurement phase in time, wherein the measurement phase and the subsequent controlling of the power supply to output the pump current to the second electrode are carried out multiple times to minimize the deviation between the electrode voltage and the specified target voltage; and
   determining the parameter of the gas mixture in the gas chamber based at least in part on the pump current.

10. The method as claimed in claim 9, wherein the sensor element comprises a heating element configured to heat the solid state electrolyte, wherein
   the heating element is controlled during the measurement phase to switch off and
   during the operating phase the heating element is controlled to set up a specified operating temperature of the solid state electrolyte.

11. The method as claimed in claim 9, wherein the parameter represents an oxygen concentration of the gas mixture.

12. The method as claimed in claim 9, wherein the gas chamber is an induction chamber of an internal combustion engine.

13. A method for detecting of a parameter of a gas mixture in a gas chamber comprising:
   disposing a sensor element in the gas chamber having first and second electrodes arranged as a planar layered structure, the first electrode and the second electrode being spaced apart along a first axis at specified intervals so that their respective edges are spaced apart from each other along the first axis and along a second axis that extends orthogonally to the respective layers and orthogonally to the first axis, are vertically offset relative to each other, and at least partly embedded in a solid state electrolyte, and that are electrically coupled to a power supply;
   a gas inlet limiter, configured such that the first electrode is acted upon indirectly via a diffusion barrier by the gas mixture of the gas chamber via the gas inlet limiter in a specified first region, the second electrode offset from the first electrode to not overlap with the first electrode, configured such that it is acted upon directly by the gas mixture of the gas chamber in another first region, and the solid state electrolyte, configured such that it is coupled to the first and second electrodes, wherein the method further comprises:

controlling the power supply during a measurement phase to switch off, detecting an electrode voltage between the first and second electrodes during the measurement phase;

determining a pump current based at least in part on a deviation of the electrode voltage from a specified target voltage during the measurement phase;

controlling the power supply to output the pump current to the second electrode of the sensor element in an operating phase that follows the measurement phase in time, wherein the measurement phase and the subsequent controlling of the power supply to output the pump current to the second electrode are carried out multiple times to minimize the deviation between the electrode voltage and the specified target voltage; and determining the parameter of the gas mixture in the gas chamber based at least in part on the pump current.

14. The method as claimed in claim 13, wherein the gas inlet limiter comprises a first diffusion barrier layer disposed such that it is coupled to the first electrode in a specified first region and the first electrode is acted upon by the gas mixture of the gas chamber via the first diffusion barrier layer only in the first region.

15. The method as claimed in claim 13, wherein the sensor element comprises a heating element configured to heat the solid state electrolyte, wherein the heating element is controlled during the measurement phase to switch off and during the operating phase the heating element is controlled to set up a specified operating temperature of the solid state electrolyte.

\* \* \* \* \*